(12) United States Patent
Ahn

(10) Patent No.: US 9,597,108 B2
(45) Date of Patent: Mar. 21, 2017

(54) MANUAL THROMBECTOMY DEVICE

(71) Applicant: Jiyong Ahn, Totowa, NJ (US)

(72) Inventor: Jiyong Ahn, Totowa, NJ (US)

( * ) Notice: Subject to any disclaimer, the term of this patent is extended or adjusted under 35 U.S.C. 154(b) by 344 days.

(21) Appl. No.: 14/319,150

(22) Filed: Jun. 30, 2014

(65) Prior Publication Data

US 2015/0005792 A1    Jan. 1, 2015

Related U.S. Application Data

(60) Provisional application No. 61/841,374, filed on Jun. 30, 2013.

(30) Foreign Application Priority Data

Dec. 30, 2013    (KR) .......................... 10-2013-0166393

(51) Int. Cl.
| | |
|---|---|
| *A61B 17/22* | (2006.01) |
| *A61B 17/3207* | (2006.01) |
| *A61B 17/221* | (2006.01) |
| *A61B 17/32* | (2006.01) |

(52) U.S. Cl.
CPC .... *A61B 17/320725* (2013.01); *A61B 17/221* (2013.01); *A61B 2017/2212* (2013.01); *A61B 2017/320012* (2013.01)

(58) Field of Classification Search
CPC .......... A61B 17/320725; A61B 17/221; A61B 2017/320012; A61B 2017/2212
See application file for complete search history.

(56) References Cited

U.S. PATENT DOCUMENTS

| | | |
|---|---|---|
| 3,828,790 A | 8/1974 | Curtiss et al. |
| 5,766,191 A | 6/1998 | Trerotola |
| 5,840,067 A * | 11/1998 | Berguer ................ A61M 25/04 604/104 |
| 6,099,534 A | 8/2000 | Bates et al. |
| 6,458,145 B1 | 10/2002 | Ravenscroft et al. |
| 8,361,095 B2 | 1/2013 | Osborne |
| 8,475,487 B2 | 7/2013 | Bonnette et al. |
| 2006/0229645 A1 * | 10/2006 | Bonnette .......... A61B 17/00234 606/159 |

FOREIGN PATENT DOCUMENTS

| | | |
|---|---|---|
| KR | 10-1303612 | 9/2013 |
| KR | 10-1332616 | 11/2013 |

* cited by examiner

*Primary Examiner* — Todd J Scherbel
*Assistant Examiner* — Son Dang
(74) *Attorney, Agent, or Firm* — Gerald E. Hespos; Michael J. Porco; Matthew T. Hespos

(57) ABSTRACT

Disclosed are manual thrombectomy devices having a plurality of elastic wires to form one or more cages and/or soft brushes connected to a lumen shaft along a longitudinal direction to easily detach thrombi from a vessel wall by manually rotating the lumen shaft right and left. And without any extra inflow tube, the manual thrombectomy device has an aspiration lumen and an inflow lumen in one body of the lumen shaft not only for preventing occurrence of a vacuum or a low pressure state in the blood vessel due to the thrombi aspiration during operation, but also for cleaning the vessel wall through outflow holes and for excreting the thrombi through aspiration holes.

15 Claims, 9 Drawing Sheets

(a) line A-A     (b) line B-B (c) enlarged view of line B-B     (d) enlarged view of line C-C (a) line A-A     (b) line D-D     (c) line E-E (a) line A-A    (b) line D-D    (c) line E-E (a) line A-A    (b) line D-D    (c) line E-E (a)    (b)    (c)    (d)

(a) line A-A (b) line F-F (a) line A-A (b) line G-G (a) line A-A　　　(b) line H-H (a) line A-A　　　(b) line I-I (a) line A-A    (b) line L-L line A-A line A-A

MANUAL THROMBECTOMY DEVICE

CROSS-REFERENCE TO RELATED APPLICATION

This application claims priority to U.S. Provisional Patent Application No. 61/841,374, filed on Jun. 30, 2013, and Korean Patent Application No. 10-2013-0166393, filed on Dec. 30, 2013, which claims priority to the former U.S. Provisional Patent Application No. 61/841,374, under 35 U.S.C. 119, the entire contents of which are hereby incorporated by reference.

BACKGROUND OF INVENTION

1. Field of the Invention

The present invention relates to thrombectomy devices, and more particularly to manual thrombectomy devices for inexpensively and easily detaching, macerating and removing thrombi organized in not only native vessels, but also graft prostheses such as arterio-venous grafts (AVG) or other vessel grafts.

2. Description of the Related Art

Not only in native vessels of a human body, but also in graft prostheses such as arterio-venous grafts or other vessel grafts used in a blood dialyses operation and the like, blood is changed into clotted masses as thrombi which are stacked or organized stubbornly to adhere to the vessel wall for interrupting blood flow and for consequently blocking the blood vessel. Therefore, various medicines and devices to remove the thrombi have been developed.

The conventional methods for removing the thrombi are largely classified into a chemical method using thrombolytic agents to dissolve clots and a physical method using devices inserting into a blood vessel such as a catheter.

The representative thrombectomy devices having developed until now are described below.

First, a commercialized AngioJet, a rheolytic thrombectomy catheter, which removes the thrombi by water jet flowed out through an outflow orifice equipped at a distal end portion of the catheter, is known.

Korean Patent No. 10-1303612 discloses a technique using a thrombus retrieving stent module equipped with a stent having a mesh member at a distal end of a push wire inserted in a micro-tube for catching and retrieving the thrombi into the inside of an expanded catheter.

U.S. Pat. No. 6,458,145 discloses a technique using three loops connected together and equipped at a distal end of a lumen shaft for catching and removing the thrombi (the loop-type similar patents are disclosed in U.S. Pat. No. 6,099,534, No. 3,828,790, etc.).

U.S. Pat. No. 5,766,191 discloses a technique using a filament cage connected by a hub at a distal end of a lumen shaft for catching and retrieving the thrombi into the inside of the lumen shaft (the cage-type similar patents are disclosed in U.S. Pat. No. 8,475,487, Korean Patent No. 10-1332616, etc.).

U.S. Pat. No. 8,361,095 discloses a technique using a thrombus engagement members disposed helically at a torsion member connected to a torque shaft located inside an inner sheath for engaging and retrieving the thrombi into the inner sheath.

The rheolytic thrombectomy catheter generally reduces the thrombectomic ability in a vessel having a large inner diameter and has the inability to remove organized and wall-adherent thrombi.

In case of the mesh or loop used to catch the thrombi and retrieve into the inside of the catheter such as Korean Patent No. 10-1303612 and U.S. Pat. No. 6,458,145, the complete removal and retrieval of the thrombi is difficult. U.S. Pat. No. 5,766,191 is the cage-type, but has similar problems as the loop-type.

In U.S. Pat. No. 8,475,487, the distal and proximal ends of a plurality of filaments are attached to each of cylindrical rings, respectively. When the plurality of filaments is expanded to form a cage, the distal end ring is proximally slid on the catheter tube because it is not fixed to the catheter tube. However, when the catheter tube is rotated to remove the thrombi, the torque is only transmitted to the expanded cage through the proximal end ring fixed to the catheter tube. Therefore, the thrombi are inefficiently removed. U.S. Pat. No. 8,475,487 has a function of the rheolytic thrombectomy catheter because a high pressure tube and a fluid jet emanator are coupled at the inside of the catheter tube. However, the high pressure tube and the fluid jet emanator have to be especially installed. Because the high pressured fluid of the fluid jet emanator is indirectly jetted through outflow orifices by proximally jetting in the inside of the catheter instead of directly jetting to the thrombi in the wall, the thrombus removing efficiency of the pressured fluid is reduced and the detached thrombi are not efficiently retrieved by inflow orifices.

Korean Patent No. 10-1332616 has cage-shaped fragmentation wires having one end connected to a control ball moving proximally and distally along a control shaft in the inside of a fragmentation shaft. When the fragmentation shaft moves distally, the fragmentation wires pressed by a sheath are expanded to a cage shape and the thrombi are removed by rotation of the fragmentation shaft. As is U.S. Pat. No. 8,475,487, the fragmentation wires only receive the torque transmitted from the one end thereof by the control ball. Thus, the thrombi are inefficiently fragmented. Because the retrieval of the fragmented thrombi is performed by suction pores disposed proximally on the sheath, the retrieval is also inefficient. When the thrombi are organized and adhered to the vessel wall, the thrombectomy effect is little if any.

U.S. Pat. No. 8,361,095 can move the fragmented thrombi by the thrombus engagement members from the blood vessel to the inside of the sheath, but it is difficult to remove the fragmented thrombi by transferring to the outside of the thrombectomy device.

SUMMARY OF THE INVENTION

To solve the problems of the conventional technology, the present invention provides manual thrombectomy devices having very simple structure for inexpensively and efficiently detaching, macerating and removing the thrombi.

To achieve the objective of the present invention, a manual thrombectomy device according to the present invention comprises: a hollow lumen shaft having a plurality of holes formed to penetrate a side of a distal end portion; a plurality of elastic wires connected to the distal end portion of the lumen shaft in a longitudinal direction of the lumen shaft to form one or more cages wrapping around the holes; and a sheath configured to wrap around the elastic wires and the lumen shaft and to move back and forth along the lumen shaft, wherein at least one end of each of the elastic wires is connected to and slides along one of wire guide tracks formed at the lumen shaft in a longitudinal direction of the lumen shaft, and wherein the sheath is configured to move back and forth along the lumen shaft for collapsing and expanding the elastic wires to the cages.

Here, both ends of each of the elastic wires may be connected to and oppositely slide along two of the wire guide tracks aligned with each other, the wire guide tracks being formed at both sides of the holes in a longitudinal direction of the lumen shaft The elastic wires may be connected to the lumen shaft for forming two or more cages in a longitudinal direction of the lumen shaft.

A soft brush may be further attached between the elastic wires of the cages.

A soft brush may be further attached to a distal or proximal portion of the elastic wires of each of the cages.

Soft brushes may be further attached to both ends of the elastic wires of each of the cages.

Each of the wire guide tracks may be configured to form a predetermined depth on an outside surface of the lumen shaft.

Each of the wire guide tracks may be configured to form a gourd shape having an inside area broader than an entrance thereof in a radial cross section of the lumen shaft, and the end of each of the elastic wires inserted into each of the wire guide tracks may be configured to form a protrusion which is not separated from the gourd shape.

Each of the wire guide tracks may be configured to form a tunnel in the lumen shaft.

Each of the wire guide tracks may be disposed at an inside surface of the lumen shaft.

Each of the wire guide tracks may be formed with a predetermined depth from an inside surface or between adjacent elastic wires on an inside surface after penetrating the wall of the lumen shaft.

Each of the elastic wires may have a longitudinal cross-sectional shape of one of a smooth, a saw tooth, a square wave and a water wave toward the outside of the cages.

An inside of the lumen shaft may be partitioned along a longitudinal direction by a predetermined separation wall into an aspiration lumen for aspirating and excreting thrombi and an inflow lumen for supplying external fluid, and the holes may be divided into aspiration holes formed at a side of a distal end portion of the aspiration lumen and outflow holes formed at a side of a distal end portion of the inflow lumen.

An aspiration means may be connected to a proximal end portion of the aspiration lumen, an inflow means may be connected to a proximal end portion of the inflow lumen, and the aspiration and inflow means may be configured in order that the same amount flows into the inflow lumen and flows out from the aspiration lumen though a radial cross-sectional area of the aspiration lumen is more than 2 times larger than that of the inflow lumen.

Each of the outflow holes may be smaller than each of the aspiration holes.

A manual thrombectomy device according to the present invention comprises: a hollow lumen shaft having a plurality of holes formed to penetrate a side of a distal end portion; a brush having soft bristles attached in a radial direction of the lumen shaft between the holes at the distal end portion of the lumen shaft; and a sheath configured to wrap around the brush and the lumen shaft and to move back and forth along the lumen shaft, wherein the sheath is configured to move back and forth along the lumen shaft for laying down and expanding the bristles of the brush, wherein each of the bristles has a predetermined size and a 'T'-shaped end, wherein the 'T'-shaped end is inserted through the wall of the lumen shaft, and wherein a stabilizer member having a small radius is inserted inside the lumen shaft.

A manual thrombectomy device according to the present invention comprises: a hollow lumen shaft having a plurality of holes formed to penetrate a side of a distal end portion; a brush having soft bristles attached in a radial direction of the lumen shaft between the holes at the distal end portion of the lumen shaft; and a sheath configured to wrap around the brush and the lumen shaft and to move back and forth along the lumen shaft, wherein the sheath is configured to move back and forth along the lumen shaft for laying down and expanding the bristles of the brush, and wherein the bristles of the brush are helically attached along the longitudinal direction of the lumen shaft on the outside or inside surface of the lumen shaft by a predetermined glue.

A manual thrombectomy device according to the present invention comprises: a hollow lumen shaft having a plurality of holes formed to penetrate a side of a distal end portion; a brush having soft bristles attached in a radial direction of the lumen shaft between the holes at the distal end portion of the lumen shaft; and a sheath configured to wrap around the brush and the lumen shaft and to move back and forth along the lumen shaft, wherein each of the bristles has a predetermined size and is connected to a flexible protruding line, and wherein the protruding line is inserted into a brush guide track having a predetermined depth on the outside surface of the lumen shaft.

The brush guide track may be configured to form a helical shape on the outside surface of the lumen shaft.

A manual thrombectomy device according to the present invention can easily detach thrombi from a blood vessel wall by manually rotating a lumen shaft right and left because a plurality of elastic wires are connected to the lumen shaft to form one or more cages longitudinally and the torque of the lumen shaft can be wholly transmitted to the elastic wires of the cages.

And because the inside of the lumen shaft is partitioned along a longitudinal direction into an aspiration lumen and an inflow lumen and a plurality of aspiration and outflow holes are formed at the opposite sides of the distal portions of the aspiration and inflow lumens, respectively, the present invention enables not only to prevent a vacuum or a low pressure state in the blood vessel due to the thrombi aspiration, but also to clean the blood vessel walls by directly shooting the externally injected fluid to the thrombi through the outflow holes without the extra inflow tube and to directly aspirate the detached thrombi into the inside of the lumen shaft through the aspiration holes in the cages and excrete to the outside.

Furthermore, the present invention can surely clean the vessel walls by brushing and detaching thrombi by one or more soft brushes attached to the lumen shaft.

In these drawings, the following reference numbers are used throughout: reference number 10 indicates a lumen shaft, 11 a radio-opaque band, 12 an aspiration hole, 13 an outflow hole, 14 and 44 wire guide tracks, 15 an elastic wire, 16 an aspiration port, 17 an inflow port, 18 an aspiration means, 19 an inflow means, 20 a sheath, 30 an oval groove, 34 a tunnel, 40 and 50 oval holes, 60 a brush (a bristle), 61 a protruding line, 62 a stabilizer member, 63 and 65 glue and 64 a brush guide track.

DETAILED DESCRIPTION

Detailed descriptions of preferred embodiments of the present invention are provided below with reference to accompanying drawings to be easily understood by those skilled in the art having ordinary knowledge in the technical field of the present invention. However, the present invention is not to be limited to the disclosed embodiments below, it is intended to be embodied to various applications based on the disclosed embodiments.

Figure 1:
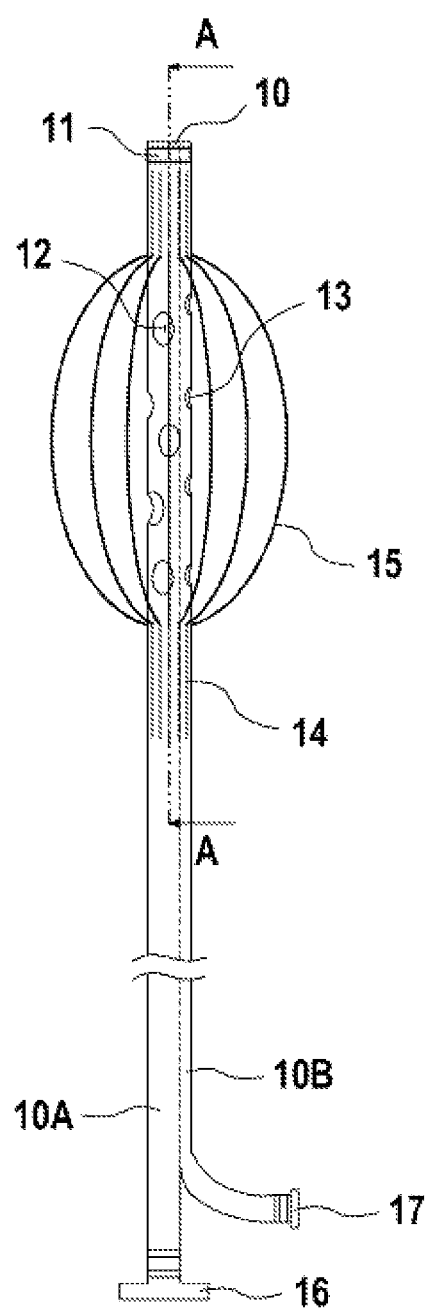
FIG. 1 is a perspective view showing a lumen shaft according to an embodiment of the present invention.
Figure 2:
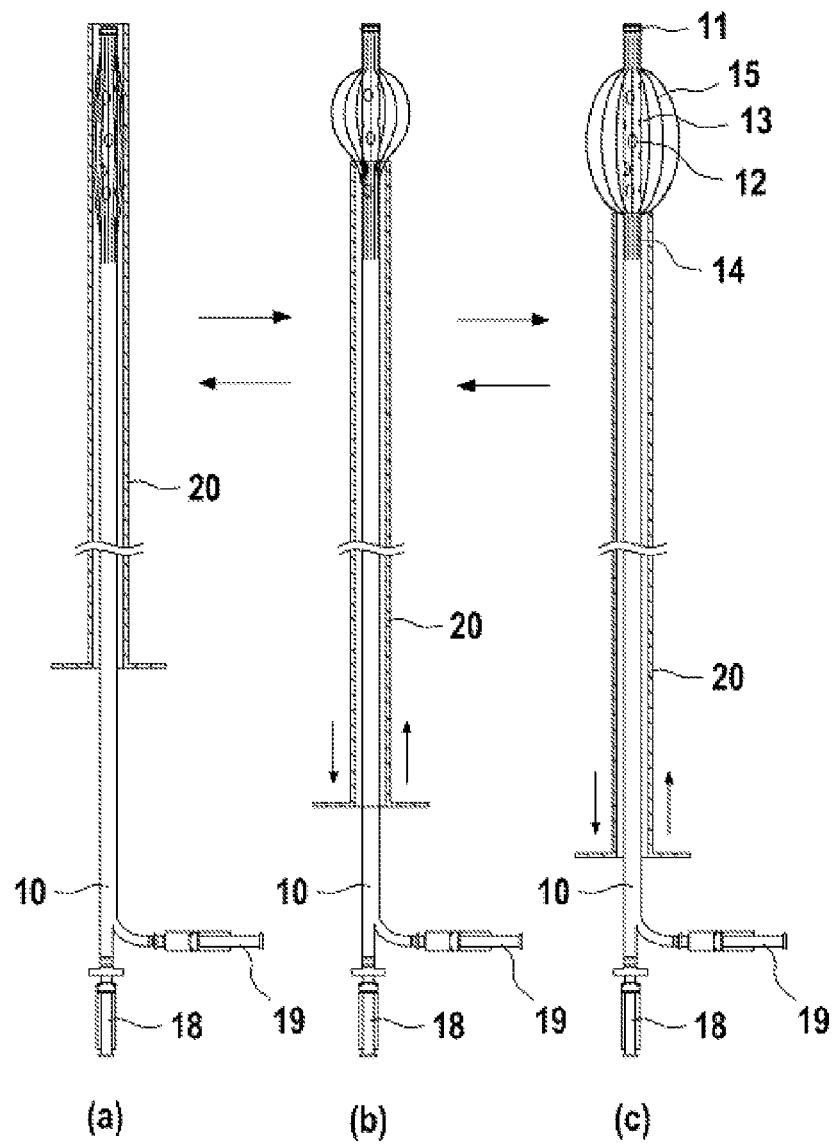
FIG. 2 is a perspective view showing a sheath wrapping around a plurality of elastic wires and the lumen shaft of FIG. 1 and the expanding structure as a cage from the collapsed elastic wires by proximal movement of the sheath and vice versa.

A manual thrombectomy device according to an embodiment of the present invention basically, as shown in FIGS. 1 and 2, comprises: a hollow lumen shaft 10 having a plurality of holes 12 and 13 formed to penetrate a side of a distal end portion; a plurality of elastic wires 15 connected to the distal end portion of the lumen shaft 10 in a longitudinal direction of the lumen shaft 10 to form one or more cages wrapping around the holes 12 and 13; and a sheath 20 configured to wrap around the elastic wires 15 and the lumen shaft 10 and to move back and forth along the lumen shaft 10, wherein at least one end of each of the elastic wires 15 is connected to and slides along one of wire guide tracks 14 formed at the lumen shaft 10 in a longitudinal direction of the lumen shaft 10, and wherein the sheath 20 is configured to move back and forth along the lumen shaft 10 for collapsing and expanding the elastic wires 15 to the cages.

Figure 4:
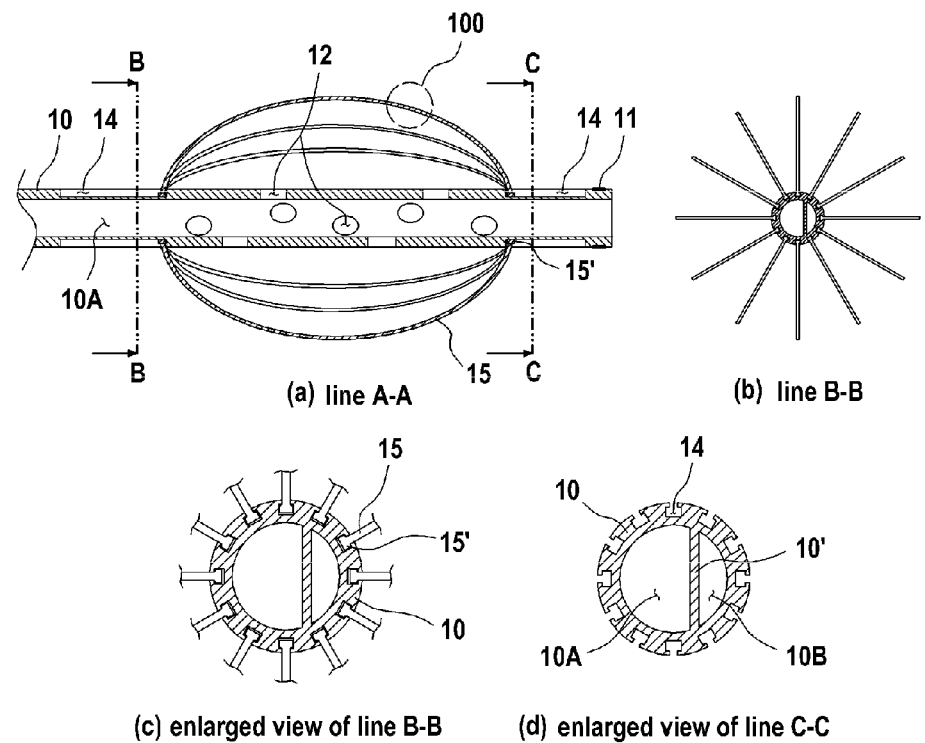
FIGS. 4 to 7 are cross sectional views showing various embodiments of wire guide tracks formed at the lumen shaft of the present invention and structures of aspiration holes and aspiration and inflow lumens through cross sectional views along line A-A of FIG. 1 (i.e., longitudinal cross-sectional views) and each of cross sectional views perpendicular to the lumen shaft (i.e., radial cross-sectional views).

Here, the lumen shaft 10 is a hollow tube formed of a well bending flexible material and interior of the lumen shaft not only has one lumen (not shown), but also, as shown in FIG. 4, is longitudinally divided by a predetermined separation wall 10' into an aspiration lumen 10A to aspirate and excrete thrombi and an inflow lumen 10B to supply an external fluid.

In the latter case, as shown in FIG. 1, the plurality of holes may be consisted of a plurality of aspiration holes 12 formed at a side of a distal end portion of the aspiration lumen 10A and a plurality of outflow holes 13 formed at a side of a distal end portion of the inflow lumen 10B. And, as shown in FIGS. 1 and 2, a predetermined aspiration means 18 may be connected through an aspiration port 16 to a proximal end portion of the aspiration lumen 10A and a predetermined inflow means 19 may be connected through an inflow port 17 to a proximal end portion of the inflow lumen 10A.

As an example shown in FIG. 4, the aspiration lumen 10A is preferably configured to have a radial cross-sectional area more than 2 times larger than that of the inflow lumen 10B and the outflow hole 13 is preferably configured to get a small size less than that of the aspiration hole 12. In consideration of the structural differences, the aspiration and inflow means 18 and 19 are preferably configured in order that the same amount flows into the inflow lumen 10B and flows out from the aspiration lumen 10A e.g., by applying different pressures to each other.

Namely, by the above mentioned configurations, when thrombi are aspirated by the aspiration means 18, a vacuum or a low pressure state in the blood vessel can be prevented. And an externally injected fluid can be jetted by high pressure through the small outflow holes 13 without an extra inflow tube just to the thrombi on vessel walls to remove the thrombi and clean the vessel walls. Then the detached thrombi can be easily aspirated through the aspiration holes 12 in the cage into the inside of the lumen shaft 10 and excreted to exterior.

On the other hand, as shown in FIG. 1, a radio-opaque band 11 to recognize the position thereof in blood vessels is disposed on the distal end of the lumen shaft 10 and a plurality of elastic wires 15 connected longitudinally to the side of the distal end portion of the lumen shaft 10 are expanded to a cage wrapping around a plurality of holes, i.e., the plurality of aspiration holes 12 and outflow holes 13.

At this time, the methods for connecting the plurality of elastic wires 15 to the lumen shaft 10 can be various, but it is preferably configured to connect both ends of each of the elastic wires 15 to the lumen shaft 10 for wholly transmitting a torque of the lumen shaft 10 to each of the elastic wires 15 during a left-right rotation. On the other hand, because each of the elastic wires 15, as shown in FIG. 2, must be collapsed inside the sheath 20 [FIG. 2(*a*)] and expanded to a cage outside the sheath 20 [FIG. 2(*c*)], at least one end thereof is preferably configured to slide along the wire guide track 14 disposed longitudinally at the lumen shaft 10.

Figure 3:
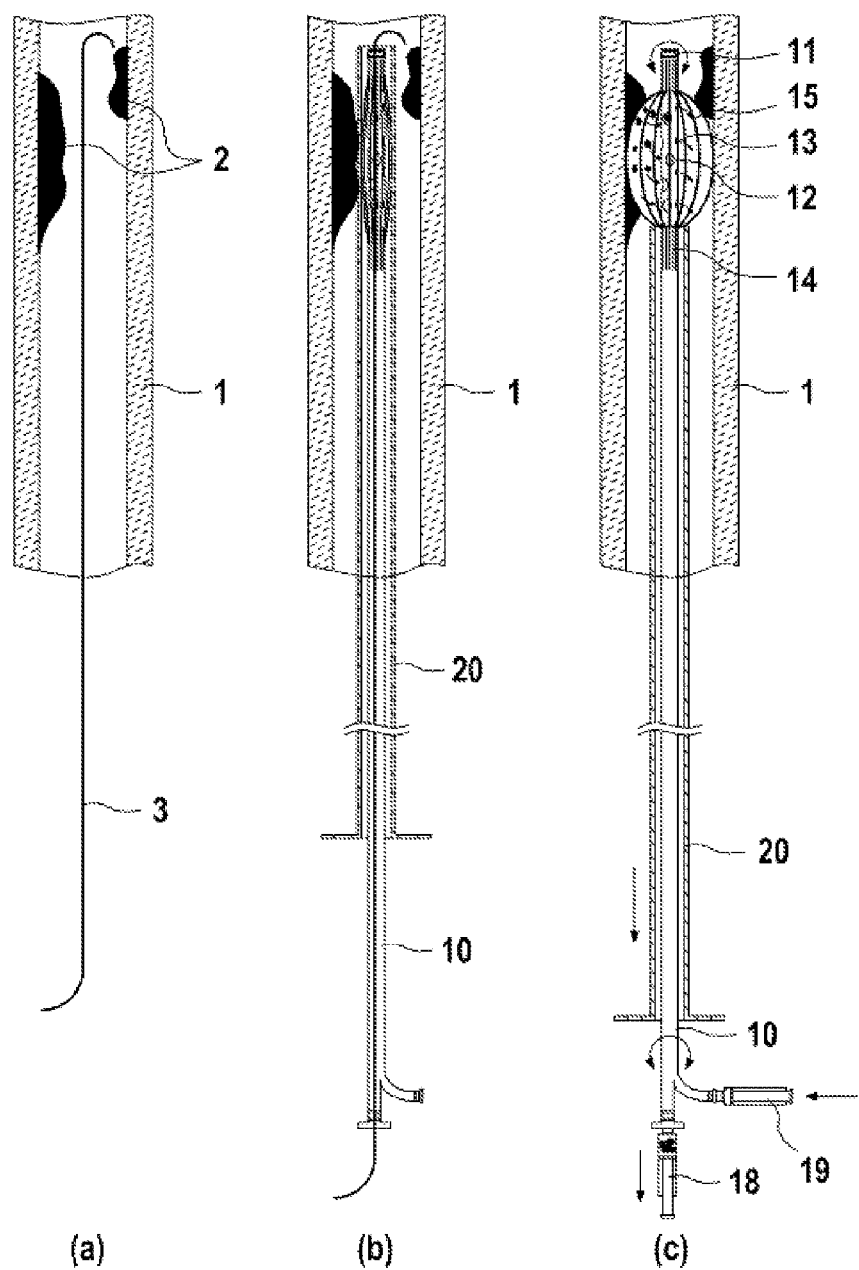
FIG. 3 is an illustration showing one example of the use of the manual thrombectomy device of FIG. 2 by inserting into the blood vessel.

As concrete embodiments for achieving the above mentioned objective of the present invention, each of the elastic wires 15 may be configured in order that one end slides along the wire guide track 14 formed at the lumen shaft 10 and the other end is inserted into and fixed to the lumen shaft 10 or also slides along the opposite wire guide track 14 aligned with the former wire guide track. FIGS. 1 to 3 are views to show the latter embodiments where the wire guide tracks 14 are formed at both sides of the holes 12 and 13 in a longitudinal direction of the lumen shaft 10.

The wire guide track 14 can be embodied in various form and the preferable embodiments are described later.

The sheath 20, as like as the lumen shaft 10, is a hollow tube formed of a well bending flexible material and, as shown in FIG. 2, is configured to wrap around the elastic wires 15 and the lumen shaft 10 and to move proximally and distally along the lumen shaft 10 for collapsing and expanding the elastic wires 15 to a cage.

Therefore, the elastic wires 15 can be made of any materials having elasticity to do the above function, preferably nitinol, platinum, titanium, stainless steel and the other elastic fibers, and more preferably shape memory alloy (SMA) changed to an original shape (for example, a shape expanded to a cage) at a predetermined temperature (for example, at a body temperature) such as nitinol which is alloyed with nickel and titanium or superelastic alloy always returned to an original shape (a cage shape) by removing the restraining force of the sheath 20.

Figure 8:
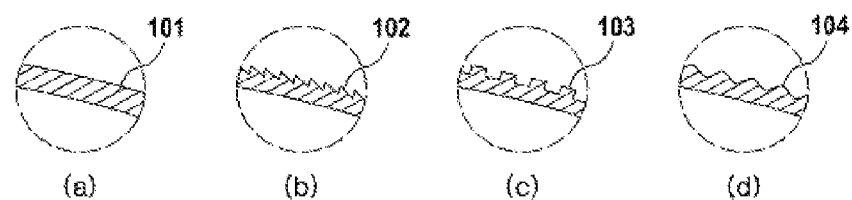
FIG. 8 is a partial enlarged view of the elastic wire shown on FIG. 4 showing examples having a longitudinal cross-sectional shape of one of a smooth, a saw tooth, a square wave and a water wave toward the outside of a cage.

Each of the elastic wires 15 may be a thin wire, as shown in FIG. 8(*a*), having a smooth shape toward the outside of a cage, i.e., no a particular protruded longitudinal cross-sectional shape (refer to a reference number 101). But it is preferable that the longitudinal cross-sectional shape of each of the elastic wires 15, as shown in FIGS. 8(*b*) to 8(*d*), is one of a saw tooth 102, a square wave 103 and a water wave 104 to increase friction effect between the thrombi on vessel walls and the wires during rotation of the lumen shaft 10.

FIG. 3 is an illustration showing one example of the use of the manual thrombectomy device according to the embodiment of FIG. 2 by inserting into a blood vessel 1 for removing thrombi 2. With reference to FIG. 3, the use and operation of the manual thrombectomy device according to the present invention are briefly described below.

First, as shown in FIG. 3(*a*), a guide wire 3 is inserted into the blood vessel 1. As shown in FIG. 3(*b*), the manual thrombectomy device 10 and 20 according to the present invention is inserted along the guide wire 3 to place a distal end portion at thrombi 2 to be removed. Next, the sheath 20 and the lumen shaft 10 are held by each of hands of an operator, respectively. As shown in FIG. 3(*c*), the sheath 20 is pulled down by one hand to expand the elastic wires 15 into a cage. In this expanded state, the lumen shaft 10 is left and right rotated by the other hand.

By the above configuration, the torque of the lumen shaft by manually applying is wholly transmitted to the elastic wires 15. The thrombi 2 attached on vessel wall are efficiently fragmented and detached without damage to the vessel wall.

The aspiration and inflow means 18 and 19 connected to a proximal end portion may be operated simultaneously with or later than the left-right rotation of the lumen shaft 10 not only for cleaning up the vessel wall by the high pressured fluid jetted from the outflow holes 13, but also for naturally collecting the thrombi 2 to the aspiration means 18 through the aspiration holes 12 and the aspiration lumen 10A without occurrence of a vacuum state or a low pressure state inside the blood vessel.

Next, with reference to FIGS. 4 to 7, the referable embodiments of the wire guide track 14 according to the present invention are described.

An embodiment according to FIG. 4 shows that the wire guide track 14 according to the present invention may be longitudinally formed at the lumen shaft 10, preferably formed as a long groove with a predetermined depth from the outside surface.

At this time, with reference to FIGS. 4(*c*) and 4(*d*), the enlarged radial cross sectional views of line B-B and line C-C, respectively, the wire guide track 14 is preferably configured to form a gourd shape having an inside area broader than an entrance thereof in a radial cross section of the lumen shaft 10, and the end of each of the elastic wires 15 inserted into each of the wire guide tracks 14 is preferably configured to form a protrusion 15' to prevent getting out of the gourd shape.

Figure 5:
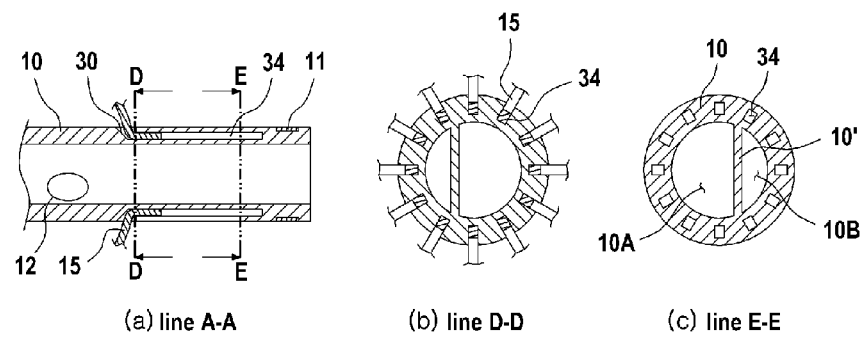

An embodiment according to FIG. 5 shows that the wire guide track according to the present invention may be formed along a longitudinal direction of the lumen shaft 10, preferably formed as a tunnel 34 in the wall connecting an oval groove 30 with a predetermined depth from outside surface.

Figure 6:
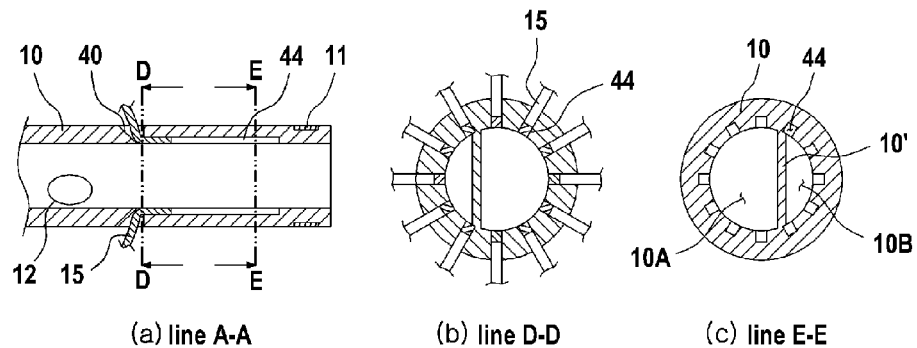
Figure 7:
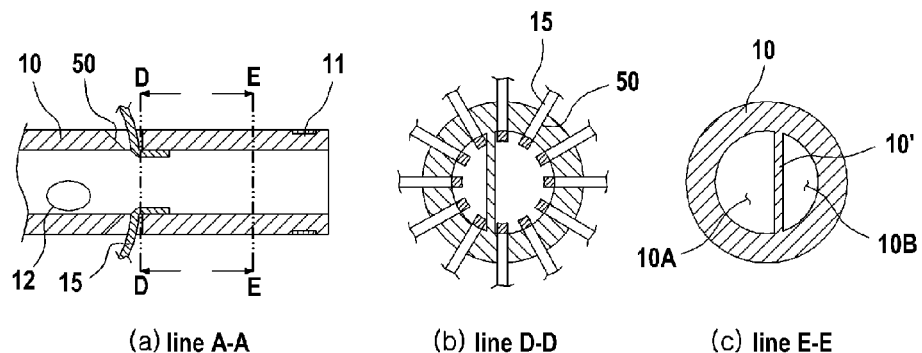

Each of embodiments according to FIGS. 6 and 7 shows that the wire guide tracks according to the present invention may be formed on the inside surface in a longitudinal direction of the lumen shaft 10. Particularly, an embodiment according to FIG. 6 shows that the wire guide tracks can be formed with oval holes 40 penetrating the wall of the lumen shaft 10 and inside grooves 44 with a predetermined depth from an inside surface. An embodiment according to FIG. 7 shows that the wire guide tracks can be configured to do not form any shapes on the inside surface, but form oval holes 50 penetrating the wall of the lumen shaft 10 and spaces made by adjacent elastic wires 15, i.e., between them on the inside surface.

Figure 9:
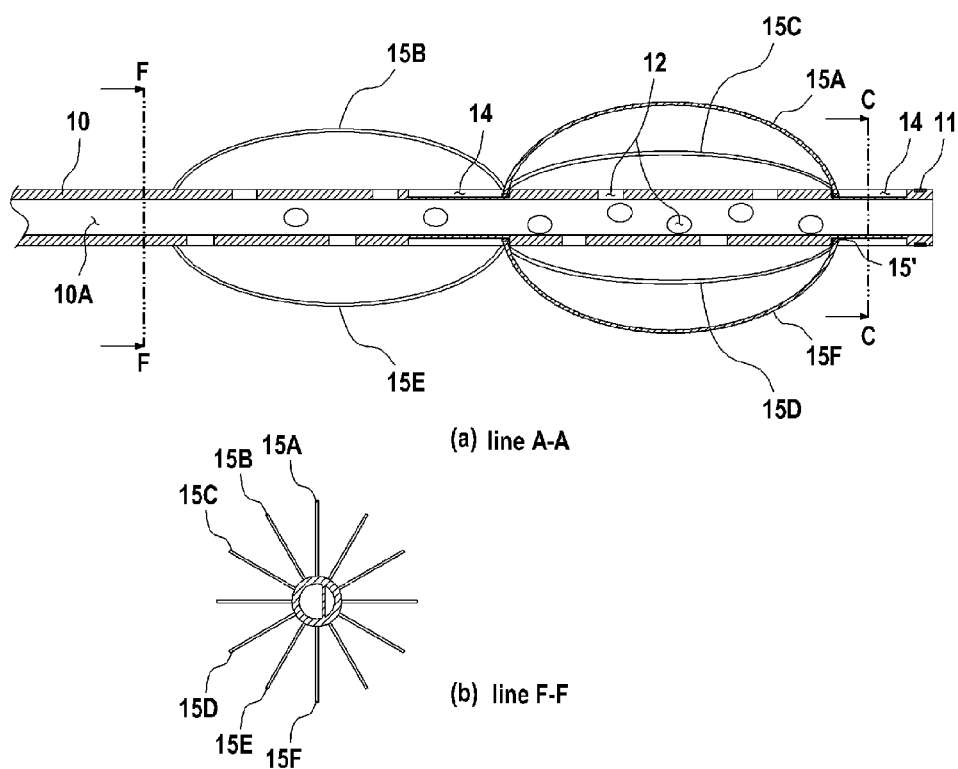
FIG. 9 is a longitudinal cross-sectional view along line A-A of FIG. 1 and a radial cross-sectional view of the lumen shaft showing an embodiment having a plurality of elastic wires for expanding to two cages at the lumen shaft of the present invention.

FIG. 9 shows an embodiment that has two cages by expanding a plurality of elastic wires 15A, 15B, 15C, 15D, 15E and 15F at the lumen shaft 10 according to the present invention. This embodiment is an application of the embodiment shown in FIG. 4. The wire guide tracks 14 of the elastic wires 15A, 15C, 15D, 15F of the distal cage and those of the elastic wires 15B, 15E of the proximal cage may be formed in a longitudinal direction of the lumen shaft 10 to have a predetermined depth from the outside surface of the lumen shaft 10, but not to overlap each other. Based on the embodiment shown in FIG. 9, the plurality of elastic wires 15 according to the present invention can be connected to the lumen shaft 10 for expanding to two or more cages in a longitudinal direction of the lumen shaft 10.

Figure 10:
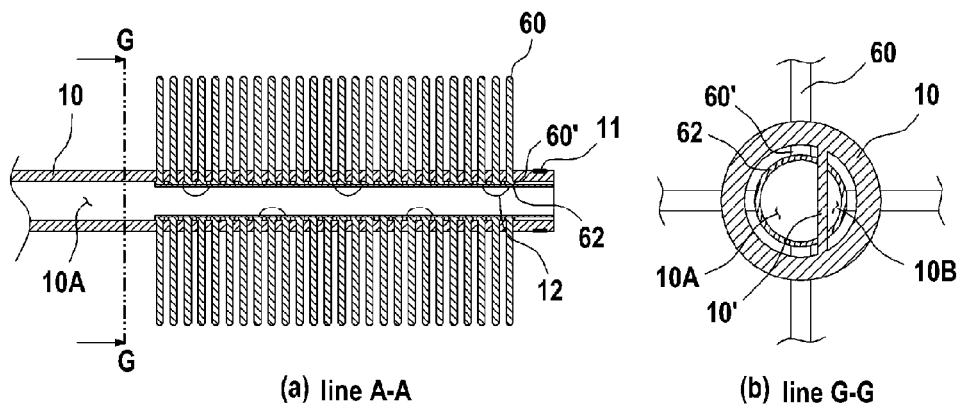
FIGS. 10 to 12 are longitudinal cross-sectional views along line A-A of FIG. 1 and radial cross-sectional views of the lumen shaft showing various embodiments having brushes made of a plurality of soft bristles instead of the plurality of elastic wires of FIG. 1 attached to the lumen shaft of the present invention.
Figure 11:
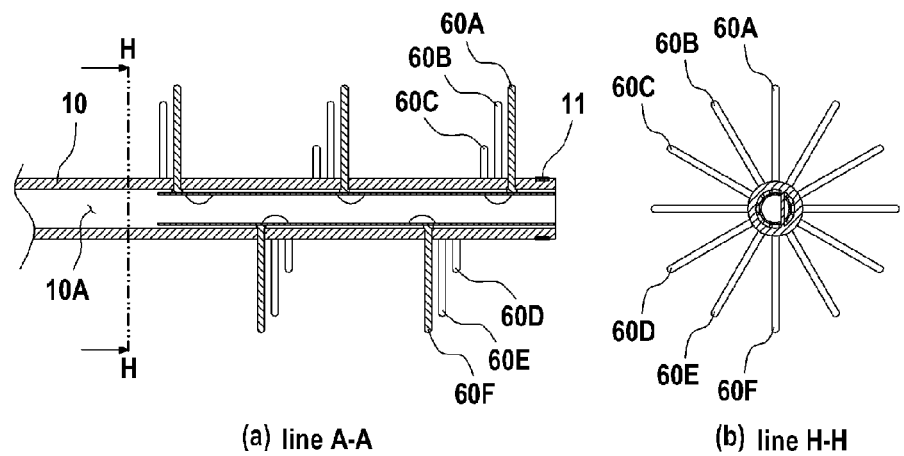
Figure 12:
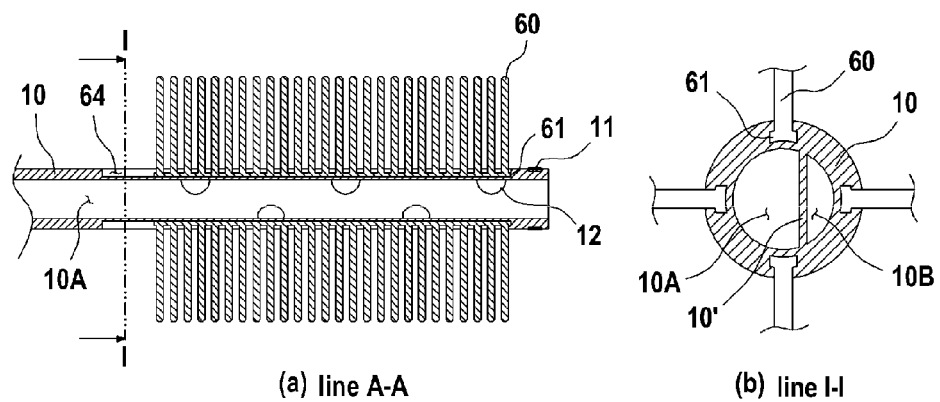

FIGS. 10 to 12 show different-shaped embodiments having brushes attached to the lumen shaft 10 according to the present invention, each of which consists of a plurality of bristles 60 instead of a plurality of elastic wires 15 shown in FIG. 1.

By this configuration, the manual thrombectomy devices according to the embodiments commonly comprise: a hollow lumen shaft 10 having a plurality of holes 12 and 13 formed to penetrate a side of a distal end portion; a brush 60 having soft bristles 60 attached in a radial direction of the lumen shaft 10 between the holes 12 and 13 at the distal end portion of the lumen shaft 10; and a sheath 20 configured to wrap around the brush 60 and the lumen shaft 10 and to move back and forth along the lumen shaft 10, wherein the sheath 20 is configured to move back and forth along the lumen shaft 10 for laying down and expanding the bristles 60 of the brush 60.

Particularly, an embodiment according to FIG. 10 shows that each of the bristles 60 has a predetermined size and a 'T'-shaped end, the 'T'-shaped end is inserted through the wall of the lumen shaft 10, and a stabilizer member 62 having small radius is inserted inside the lumen shaft 10 to fix the bristles 60. In this case, brushes are drawn as a cross shape because a plurality of holes 12 and 13 are formed at the lumen shaft 10 which is not attached with the brushes, but brushes can be attached as a multi-leaf type having more than 4.

FIG. 11, unlike the embodiment shown in FIG. 10, shows an embodiment having a brush with bristles 60A, 60B, 60C, 60D, 60E and 60F attached helically along a longitudinal direction of the lumen shaft 10 by a stabilizer member. The bristles are also attached on the outside or inside surface of the lumen shaft 10 by a predetermined glue.

FIG. 12 shows an embodiment that each of the bristles 60 has a predetermined size and is connected to a flexible protruding line 61 as a body and the protruding line 61 is inserted into a brush guide track 64 having a predetermined depth on the outside surface of the lumen shaft 10. At this time, the brush guide track 64, as the wire guide track 14 of the embodiment shown in FIG. 4, is preferably formed with a gourd shape in a radial cross sectional view and the protruding line 61 is preferably installed into the brush guide track 64 by an inserting method.

Embodiments according to FIGS. 13 to 17 are showing that it is possible to variously embody by combining the elastic wires 15 for cages with soft brushes 60 at the lumen shaft 10 of the present invention.

Figure 13:
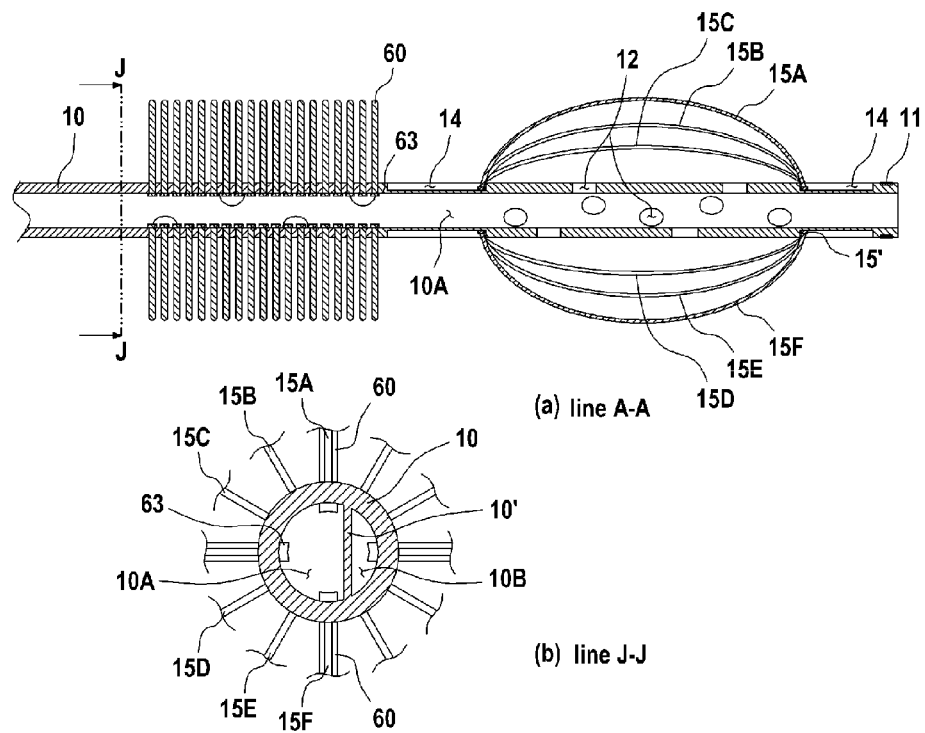
FIGS. 13 to 17 are longitudinal cross-sectional views along line A-A of FIG. 1 and/or radial cross-sectional views of the lumen shaft showing various embodiments having the elastic wires of the cage and the soft brushes connected to the lumen shaft of the present invention.

In other words, an embodiment shown in FIG. 13 shows that soft brushes 60 can be further attached at the proximal portion spaced out a wire guide track 14 from a cage of the elastic wires 15. Here, an example shows that the bristles 60 are attached to the inside surface of the lumen shaft 10 by a predetermined glue 63, but the other methods can be used to attach.

Figure 14:
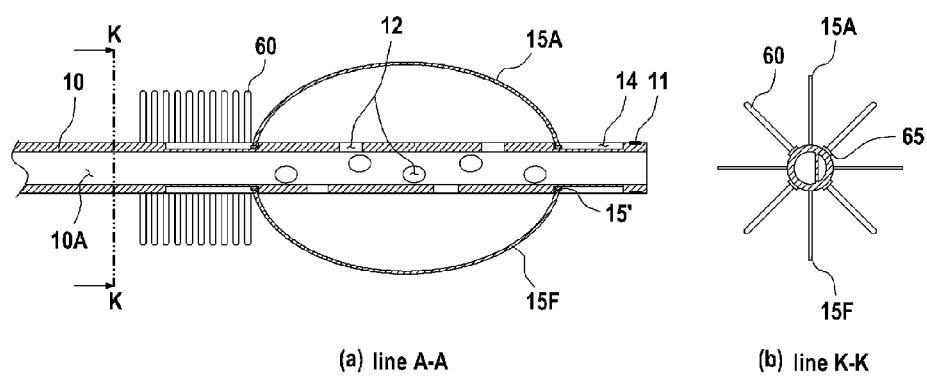

An embodiment according to FIG. 14 shows that soft brushes 60 can be further attached just at the proximal end of a cage of the elastic wires 15. In this case, unlike the embodiment shown in FIG. 13, it shows that the brushes 60 can be longitudinally attached at between angles of the elastic wires 15 and the bristles can be also attached to the outside surface of the lumen shaft 10 by a predetermined glue 63.

Figure 15:
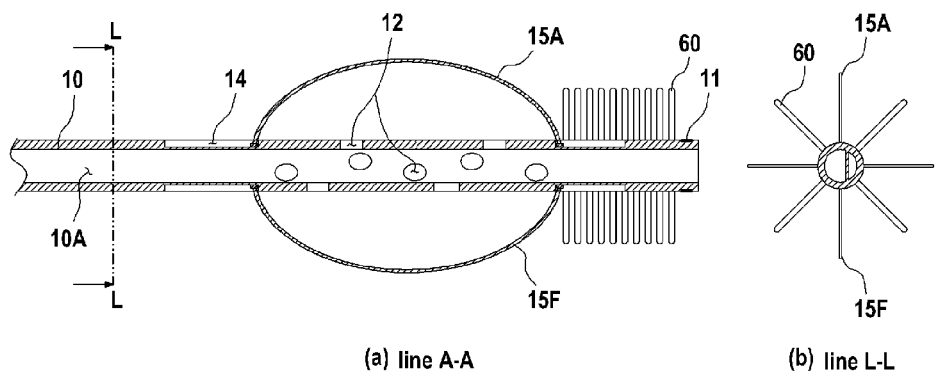

An embodiment according to FIG. 15, on the contrary to FIG. 14, shows that soft brushes 60 can be further attached just at a distal end of a cage of the elastic wires 15.

Figure 16:
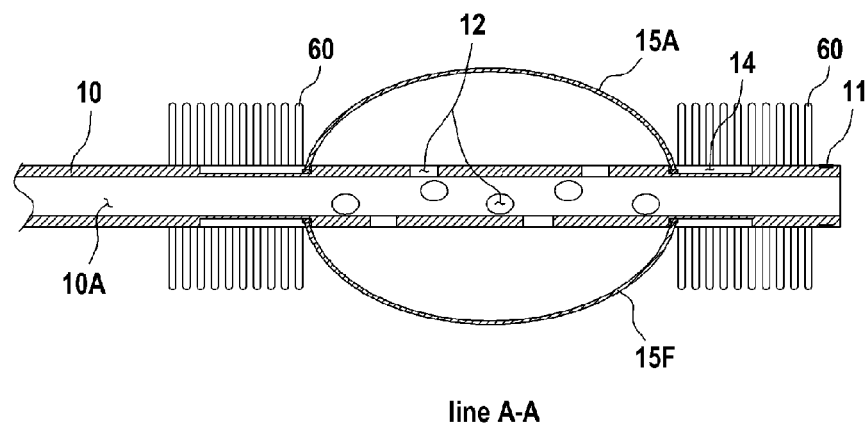

An embodiment according to FIG. 16 shows that soft brushes 60 can be further attached just at both ends of a cage of the elastic wires 15.

Figure 17:
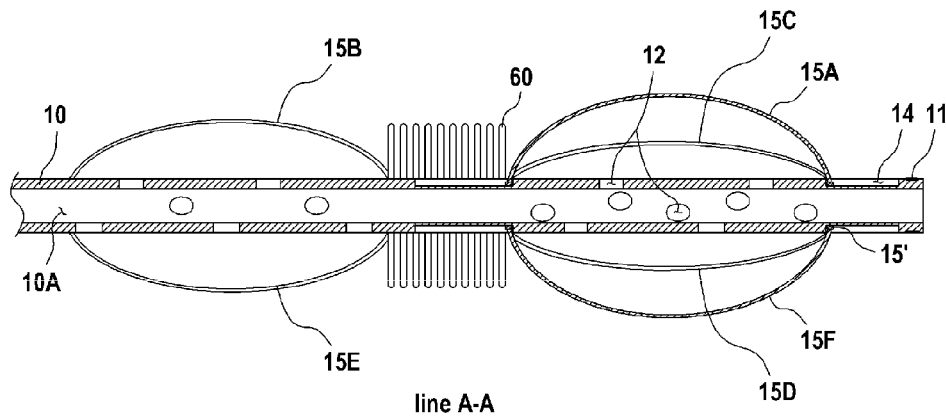

Finally, an embodiment according to FIG. 17 shows that soft brushes 60 can be further attached between two cages of the elastic wires 15.

The bristle length of the above mentioned brushes, as shown in FIG. 13, is preferably the maximum spaced length (i.e., the maximum expanding distance) from the lumen shaft 10 when the elastic wires 15 expanded to a cage. The bristles may be made of the same materials as the elastic wires 15, but it is preferable that the bristles are made of the materials easier transformed and greater restored to the original shapes than the elastic wires 15. Therefore, 'soft brush' in the present specification is used to indicate a relative concept that it transforms easier and restores to the original shape better than the elastic wire 15.

As the above mentioned, when soft brushes 60 are further configured at the lumen shaft 10 according to an embodiment of the present invention, it is also possible to very clean vessel walls by brushing and detaching thrombi.

What is claimed is:

1. A manual thrombectomy device comprising:
a hollow lumen shaft having a plurality of holes formed to penetrate a side of a distal end portion;
a plurality of elastic wires connected to the distal end portion of the lumen shaft in a longitudinal direction of the lumen shaft to form one or more cages wrapping around the holes; and
a sheath configured to wrap around the elastic wires and the lumen shaft and to move back and forth along the lumen shaft,
wherein both ends of each of the elastic wires are at least one end of each of the elastic wires is connected to and oppositely slide along two of wire guide tracks formed at the lumen shaft in a longitudinal direction of the lumen shaft, the wire guide tracks being aligned with each other and being formed at both sides of the holes in a longitudinal direction of the lumen shaft, and
wherein the sheath is configured to move back and forth along the lumen shaft for collapsing and expanding the elastic wires to the cages.

2. The manual thrombectomy device of claim 1,
wherein the elastic wires is connected to the lumen shaft for forming two or more cages in a longitudinal direction of the lumen shaft.

3. The manual thrombectomy device of claim 2,
wherein a soft brush is further attached between the elastic wires of the cages.

4. The manual thrombectomy device of claim 1,
wherein a soft brush is further attached to a distal or proximal portion of the elastic wires of each of the cages.

5. The manual thrombectomy device of claim 1,
wherein soft brushes are further attached to both ends of the elastic wires of each of the cages.

6. The manual thrombectomy device of claim 1,
wherein each of the wire guide tracks is configured to form a predetermined depth on an outside surface of the lumen shaft.

7. The manual thrombectomy device of claim 1,
wherein each of the wire guide tracks is configured to form a tunnel in the lumen shaft.

8. The manual thrombectomy device of claim 1,
wherein each of the wire guide tracks is disposed at an inside surface of the lumen shaft.

9. The manual thrombectomy device of claim 8,
wherein each of the wire guide tracks is formed with a predetermined depth from an inside surface or between adjacent elastic wires on an inside surface after penetrating the wall of the lumen shaft.

10. The manual thrombectomy device of claim 1,
wherein each of the elastic wires has a longitudinal cross-sectional shape of one of a smooth, a saw tooth, a square wave and a water wave toward the outside of the cages.

11. The manual thrombectomy device of claim 1,
wherein an inside of the lumen shaft is partitioned along a longitudinal direction by a predetermined separation wall into an aspiration lumen for aspirating and excreting thrombi and an inflow lumen for supplying external fluid, and
wherein the holes are divided into aspiration holes formed at a side of a distal end portion of the aspiration lumen and outflow holes formed at a side of a distal end portion of the inflow lumen.

12. The manual thrombectomy device of claim 11,
wherein an aspiration means is connected to a proximal end portion of the aspiration lumen,
wherein an inflow means is connected to a proximal end portion of the inflow lumen, and
wherein the aspiration and inflow means are configured in order that the same amount flows into the inflow lumen and flows out from the aspiration lumen though a radial cross-sectional area of the aspiration lumen is more than 2 times larger than that of the inflow lumen.

13. The manual thrombectomy device of claim 12,
wherein each of the outflow holes is smaller than each of the aspiration holes.

14. A manual thrombectomy device comprising: a hollow lumen shaft having a plurality of holes formed to penetrate a side of a distal end portion; a plurality of elastic wires connected to the distal end portion of the lumen shaft in a longitudinal direction of the lumen shaft to form one or more cages wrapping around the holes; and a sheath configured to wrap around the elastic wires and the lumen shaft and to move back and forth along the lumen shaft, wherein at least one end of each of the elastic wires is connected to and slides along one of wire guide tracks formed at the lumen shaft in a longitudinal direction of the lumen shaft, and wherein the sheath is configured to move back and forth along the lumen shaft for collapsing and expanding the elastic wires to the cages, each of the wire guide tracks is configured to form a predetermined depth on an outside surface of the lumen shaft and to form a gourd shape having an inside area broader than an entrance thereof in a radial cross section of the lumen shaft, and wherein the end of each of the elastic wires inserted into each of the wire guide tracks is configured to form a protrusion which is not separated from the gourd shape.

15. The manual thrombectomy device of claim 1,
   wherein both ends of each of the elastic wires are connected to and oppositely slide along two of the wire guide tracks aligned with each other, the wire guide tracks being formed at both sides of the holes in a longitudinal direction of the lumen shaft.

* * * * *